United States Patent [19]

Shanley et al.

[11] Patent Number: 5,685,864
[45] Date of Patent: Nov. 11, 1997

[54] LOCKING DEVICE FOR ASPIRATOR, SYRINGE OR LIKE INSTRUMENT

[75] Inventors: Laurence M. Shanley; Hubert Menendez, both of Miami, Fla.

[73] Assignee: Interventional Research Technologies, Miami, Fla.

[21] Appl. No.: 490,348

[22] Filed: Jun. 14, 1995

Related U.S. Application Data

[63] Continuation-in-part of Ser. No. 259,875, Jun. 15, 1994, abandoned, which is a continuation-in-part of Ser. No. 155,390, Nov. 22, 1993, abandoned.

[51] Int. Cl.$^6$ .................................................. A61M 5/00
[52] U.S. Cl. ........................ 604/211; 604/187; 604/207; 604/224
[58] Field of Search ................................ 604/15–18, 38, 604/68, 181, 187, 188, 218, 191, 220, 221, 223, 224, 207, 208–211, 214, 227, 228

[56] References Cited

U.S. PATENT DOCUMENTS

| | | |
|---|---|---|
| 913,297 | 2/1909 | Krautschneider . |
| 1,393,720 | 10/1921 | Lomas et al. . |
| 3,831,603 | 8/1974 | Armenti . |
| 3,938,505 | 2/1976 | Jamishidi . |
| 4,386,606 | 6/1983 | Tretinyak . |
| 4,562,844 | 1/1986 | Carpenter . |
| 4,635,792 | 1/1987 | Yamada et al. . |
| 4,711,637 | 12/1987 | Leigh et al. . |
| 4,747,484 | 5/1988 | Ackeret . |
| 4,758,232 | 7/1988 | Chak . |
| 4,807,749 | 2/1989 | Ackeret . |
| 4,810,249 | 3/1989 | Haber et al. . |
| 4,875,578 | 10/1989 | Nehl . |
| 5,011,010 | 4/1991 | Francis et al. . |
| 5,049,135 | 9/1991 | Davis . |
| 5,135,111 | 8/1992 | Stoeger . |
| 5,213,209 | 5/1993 | Song . |
| 5,306,258 | 4/1994 | de la Fuente . |

FOREIGN PATENT DOCUMENTS

| | | |
|---|---|---|
| 0208975 | 1/1987 | European Pat. Off. . |

Primary Examiner—Mark Bockelman
Assistant Examiner—N. Kent Gring
Attorney, Agent, or Firm—Herbert L. Lerner; Laurence A. Greenberg

[57] ABSTRACT

An aspirator assembly enabled to remove fluids from a patient comprises an elongated hollow interior barrel, a plunger reciprocally movable within the barrel along the length thereof and extending outwardly from a rear end of the barrel. The plunger includes an elongated stem having a grip at an outer end thereof and a plunger head secured to an inner end of the stem. The plunger head is slidably engagable with an interior surface of the barrel. The improvement is found in a locking device which is selectively positionable into and out of a locked position. The locking device is formed in part on both the barrel and the stem and is adapted for removably locking the plunger head in a plurality of spaced apart locations within and along the length of the barrel. Additionally, the stem may be rotated so as to disengage the locking device and provide an aspirator with unobstructed reciprocation. Furthermore, a threaded stem connects the plunger head to the main plunger stem, so as to allow accurate adjustment of the aspirator volume by turning the handle. A flow control valve is provided at the second end of the barrel which allows selective closing of the end.

23 Claims, 4 Drawing Sheets

LOCKING DEVICE FOR ASPIRATOR, SYRINGE OR LIKE INSTRUMENT

CROSS-REFERENCE TO RELATED APPLICATION

This is a continuation-in-part of my application Ser. No. 08/259,875, filed Jun. 15, 1994 abandoned; which was a continuation-in-part of application Ser. No. 08/155,390, filed Nov. 22, 1993, now abandoned.

BACKGROUND OF THE INVENTION

1. Field of the Invention

The invention relates to a locking structure adapted to be used on and incorporated in an aspirator, syringe or like instrument wherein the plunger of the aspirator may be locked into any one of a plurality of positions as it is withdrawn in the inside of the barrel of the aspirator, syringe, etc. The technician will therefore be able to maintain a negative pressure within the barrel by lockingly positioning the plunger at any one of a plurality of given locations such as when fluid is being withdrawn from the body.

2. Description of the Related Art

In the use of aspirators it is commonly known in the medical profession that the maintenance of a certain amount of negative pressure within the barrel of the aspirator or syringe type structure is required and necessary. Various common place methods have been utilized in actual practice including, but not limited to, a clamping tool or the like being somehow secured to the exterior of the plunger as it is being withdrawn. Return of the plunger, which would normally occur due to the negative pressure within the barrel of the syringe or aspirator, is prevented by the presence and blocking engagement of the clamping tool.

In addition certain patented inventions, as evidenced by the following United States patents have recognized the problem and attempted to solve it. For example, the U.S. Pat. No. 4,562,844 to Carpenter discloses a multipurpose syringe for obtaining a blood sample and for storing and shipping the sample. An elonged plunger rod 36 has a locking device 40, 42, 56, etc. located on one end thereof adjacent to a plunger 32. A cap as at 44 (FIG. 1) is fitted over the open outer end of the barrel 10. This cap has an opening which allows the free passage of the two spaced support flanges 40 and 42 to normally pass therethrough (FIG. 5) however, when the rod and accordingly the flanges attached thereto are rotated, the two passages 56 become positioned out of alignment with two inward projections 54. The flanges are therefor not allowed to pass through the hole since the passages 56 and the projections 54 are not in alignment. The plunger is maintained in its outermost position when this occurs. Rotation of the rod or plunger such that the passages 56 align with the projections 54 allows the flanges to pass through the hole in the cap 54 and further allows the plunges to pass back into the interior of the barrel.

The U.S. Pat No. 4,711,637 to Leigh includes a removable clip type structure shown in detail in FIG. 6 which when placed on the flange 34 of the outer most end of the barrel will engage or come into interference with a portion of the plunger rod thereby locking it into a preferred position.

The U.S. Pat. No. 4,758,232 to Tretinyak discloses a locking means integrally formed on a somewhat inner end of the plunger rod and includes two outwardly extending fingers 14 and attendant projecting recesses as best shown as FIG. 7, it appears that a rotation of the rod is necessary to accomplish its locking position in the outwardly extending orientation of FIG. 7.

The U.S. Pat. No. 5,095,914 to Sarstedt discloses a blood extraction device with a one way piston movement wherein a piston rod 14 is secured to a piston 15 at a forward end of the piston rod and is arranged to slide axially within the cylinder 11. The piston can essentially be moved only in the direction away from the forward end of the extraction cylinder 11 and is practically incapable of being moved when subjected to a force in the direction of the forward end due to one way coating means of prevention 17 and 18. FIG. 1 discloses details including a linear array of outwardly projecting teeth or gear like members 16 serving to react with lock or stop member 17 attached to a plug secured within the outer end of the cylinder 11. The device apparently is not meant to reciprocally move the plunger 15 or the attached rod 14 in either direction within the cylinder, but to always hold the rod in an outer most position once it is placed in such position.

The structures disclosed in the above noted patents are representative of attempts in the prior art to accomplish the locking of a plunger associated with an aspirator, syringe, etc. in a desired position primarily for purposes of maintaining a negative pressure within the interior of the barrel of the aspirator. While such structures are soon to be operable there is still a need in terms of practical use in the medical profession for a more efficient and effective means of accomplishing such locking or maintenance of the plunger in a given position while a negative pressure is maintained within the barrel of the aspirator.

It is an additional object of the invention to provide an aspirator syringe which may be pre-biased in terms of the vacuum prior to contact with the patient. Also, it is yet another object to provide such a syringe which is suitable for draining.

SUMMARY OF THE INVENTION

With the foregoing and other objects in view there is provided, in accordance with the invention, an improvement in an aspirator assembly of the type having an elongated hollow barrel with a first open end and a second open end adapted to be attached at an auxiliary device; a plunger received in the hollow barrel through the first open end and being reciprocatingly movable within the barrel; the plunger including an elongated stem and a plunger head attached to the stem and being slidably disposed in sealing engagement with an interior surface of the barrel. The improvement comprises: locking means for selectively locking the elongated stem and the plunger head in any one of a plurality of spaced-apart positions along a length of the barrel.

In accordance with another feature of the invention, the locking means include a stop member attached to the barrel and locking tabs integrally formed on the elongated stem, and wherein the plunger is rotatable relative to the barrel so as to move the stop member and one of the tabs into a locking position thereof.

In other words, the present invention relates to an aspirator assembly of the type used to remove fluids from the human body the assembly comprises a syringe type structure having an elongated hollow interior barrel with a needle or like supplementary device attached to one open end thereof and wherein the barrel includes a second open end through which an elongated plunger is mounted to the barrel on the interior thereof. More specifically the plunger includes an elongated stem having a length somewhat longer than the length of the barrel. The stem further includes a plunger head secured to an outer most end thereof. This plunger head in conventional fashion is adapted for a reciprocal movement within the interior of the hollow barrel and also is structured to sealingly engage yet slidelingly move relative to the interior surfaces of the barrel. The outer most end of the stem includes a gripping end for hand manipulation of the stem to accomplish its reciprocal movement within the barrel. In the conventional mode of operation the needle, attached to the barrel is inserted into the human body. The plunger is then retracted such that the plunger head is drawn slowly upwardly toward the outermost end of the barrel or toward the end to which the needle is attached. As should be obvious, a negative pressure then develops within the barrel as the fluid is drawn from the human body into the interior of the barrel. It is desirable during such an operation for the stem to be located or maintained at a fixed location such that the fluid withdrawn will remain in the barrel under negative pressure rather than be forced back in the body, which would happen if the stem were released.

Therefore the present invention is more specifically directed to a locking assembly associated with the subject aspirator assembly. The subject locking means includes a plurality of flanges formed on the stem in spaced relation to one another wherein each of the flanges includes an opening or aperture intricately formed therein. The flanges naturally extend transversely outward from the stem towards the interior surface of the barrel. The locking means further includes a stop member secured to the inner surface of the barrel and a movable therewith relative to the stem. The dimension and configuration, as well as the disposition of the stop member is such as to cooperate with the size of the opening in each of the plurality of flanges. To this end when any one of the openings in any one of the plurality of flanges is in alignment with the stop member, the stop member may pass therethrough such that the stem may be moved literally along the length of the barrel either toward a totally inwardly directed position or an outwardly extended or retracted position.

To the contrary, a locked position of the stem in any one of the plurality of positions may occur by rotation of the stem including the plunger head within the interior if the barrel such that a solid portion of any one of the flanges may be disposed in an abutting engagement or interfering relation to the stop member. But by virtue of the disposition of such solid portion of any one of the flanges, such a solid portion would in fact engage the stop member and prevent linear movement of the stem within the barrel.

Since there is a vacuum developed within the interior of the barrel as the fluid is withdrawn from the human body or applicable instrumentation, there is a natural bias or force extended on the plunger head so as to move it towards the bend to which the needle is attached. A locked position of the locking means, as defined above, is when the stem is rotated such that a solid portion of an adjacently positioned one of the flanges or stop members is disposed into engagement and/or into aligned relation and eventually engagement with the stop member. The stop member is thereby disposed between the solid portion of any one of the adjacently positioned plurality of flanges and the plunger head. This will serve to effectively lock the plunger head in a given position and prevent its movement towards the end of the barrel to which the needle is attached.

Another feature of the present invention is the number and location of each of the above noted flanges defining in part the locking means. In one embodiment the plurality of flanges are at least two in number wherein a first of the flanges is located substantially adjacent the plunger head such that the plunger may be maintained in a locked position adjacent the second open end of the barrel or the open end through which the plunger head passed during initial assembly. The second of such plurality of flanges is located substantially midportion along the length of the stem such that the plunger head may be locked into as position substantially midway along the length of the barrel in the first instance the fluid will substantially fill the entire barrel.

In the second aforementioned embodiment a larger number of flanges defines the plurality of flanges such that the flanges are spaced a predetermined equal distance from one another. This predetermined distance is such that the plunger head may be locked on any one of a plurality of positions along the length of the interior of the barrel wherein such positions of locked disposition of the plunger head equivalent to substantially a cubic centimeter of fluid being drawn into or removed from the interior of the barrel of the subject aspirator assembly.

The stop valve or check valve at the forward end of the barrel (the luer lock end to which the needle or another auxiliary device is attached) allows pre-biasing of the aspirator assembly without having to subject the patient to further discomfort which the vacuum is applied and the aspirator is locked. This is particularly advantageous in the context of draining.

In that context, the drain conduit is a further advantageous feature which allows constant draining far beyond the capacity of the aspirator barrel. In that case, the medical worker simply applies new vacuum, when the earlier vacuum has been lost when a certain amount has been drained.

Other features which are considered as characteristic for the invention are set forth in the appended claims.

Although the invention is illustrated and described herein as embodied in a locking device for an aspirator, a syringe or like instrument, it is nevertheless not intended to be limited to the details shown, since various modifications and structural changes may be made therein without departing from the spirit of the invention and within the scope and range of equivalents of the claims.

The construction of the invention, however, together with additional objects and advantages thereof will be best understood from the following description of the specific embodiment when read in connection with the accompanying drawings.

DESCRIPTION OF THE PREFERRED EMBODIMENTS

Figure 1:
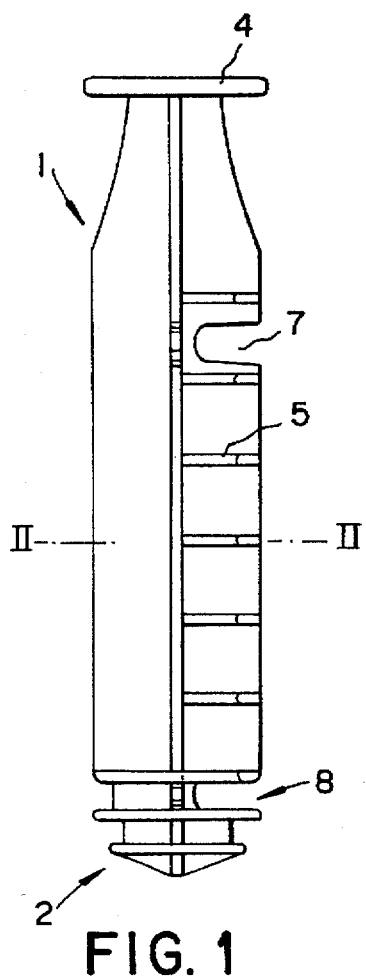
FIG. 1 is a front-elevational view of a plunger according to the invention.
Figure 3:
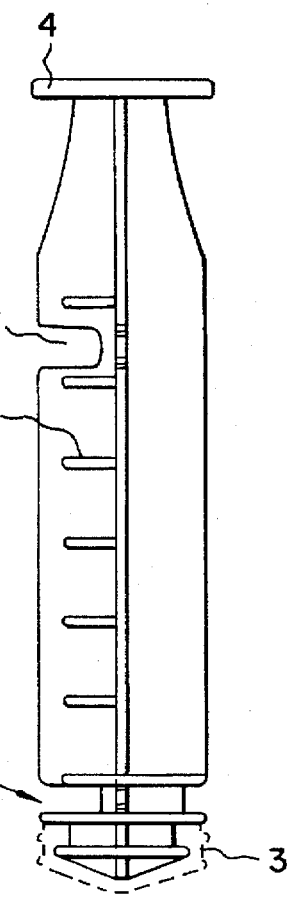
FIG. 3 is a rear-elevational view of the plunger of FIG. 1 with a plunger seal illustrated with dashed lines.
Figures 4, 6:
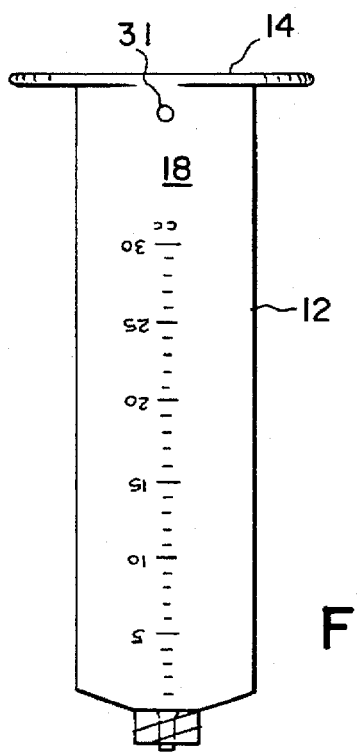
FIG. 4 is an elevational view of a barrel for receiving the plunger.
FIG. 6 is a top-plan view of the barrel with an inserted plunger and a locking pin.

Referring now to the figures of the drawing in detail and first, particularly, to FIGS. 1 and 4 thereof, there is seen an aspirator plunger generally indicated as 1. The plunger is to be inserted in an elongated barrel as at 12 which has a hollow interior and which includes a first open end generally indicated as 14 and a second open end generally indicated as 16. The second open end is a luer lock adapted to receive some type of needle or other auxiliary device, which facilitates access into the human body for the removal of fluids therefrom. In that respect, the aspirator is also suitable as a dispensing means, for instance to be tied into an IV system and to be connected to an IV adapter port. The luer lock of this invention has been improved over comparable devices of the prior art. Firstly, the male pin has been reinforced at the base with additional material, so that the pin cannot break off as easily as those of the prior art. Secondly, the pin has been shortened. This allows the end attached hose or aspirator tube to sit directly on the end wall of the barrel 12, which also provides improved strength. The improved system is safely able to be utilized for positive pressures of about 16 atm (300 psi).

The first open end 14 is disposed in direct communication with the hollow interior 18 of the barrel and is further dimensioned and otherwise adapted to facilitate the insertion of the elongated stem of the plunger 1. The plunger 1 has a plunger head 2 secured to an inner-most end thereof. The open end 14 of course is large enough to allow insertion of the plunger head such that the plunger head 2 is reciprocally movable along the length of the interior 18 of the barrel 12.

The plunger head 2 is conventionally provided with one or more seals 3 to facilitate slidable but sealing engagement with an interior surface of the barrel 12. The opposite end of the plunger 1 includes some type of gripping structure as at 4 to facilitate the linear and reciprocal movement of the plunger and particularly the plunger head 22 within the hollow interior 18 of the barrel 12.

An important feature of the present invention is the existence of a locking means on the subject aspirator assembly. The locking means is formed by the cooperation of mutually spaced-apart flanges 5 formed along a rib of the plunger stem and at least one stop member 30 which is secured to the barrel so as to protrude into the interior 18 of the barrel 12 and to mesh with the flanges 5 of the inserted plunger 1. The stop member 30, formed as a locking pin 30, is removable from the aspirator body. Logically, the opening 31 is not a problem, because it is always disposed behind the plunger head 3.

Figure 2:
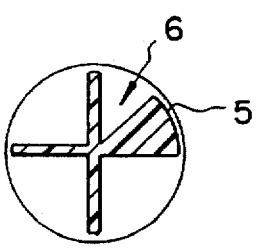
FIG. 2 is a sectional view taken along the line II—II in FIG. 1.

Particularly with reference to FIG. 2, the plunger i is somewhat rotatable within the interior 18 of the barrel 12 to the extent that either the solid portion 5 (the flange) or the opening or aperture of each locking flange 5 is selectively positioned into alignment with the stop member 30. When the opening 6 is positioned into alignment with the stop member 30, the plunger 1 and accordingly the plunger head 2 is allowed to move freely within the interior of the barrel 12 between a fully extracted position and a fully inserted position. The plunger assumes the latter position immediately prior to the fluid being withdrawn from the human body.

Figure 7:
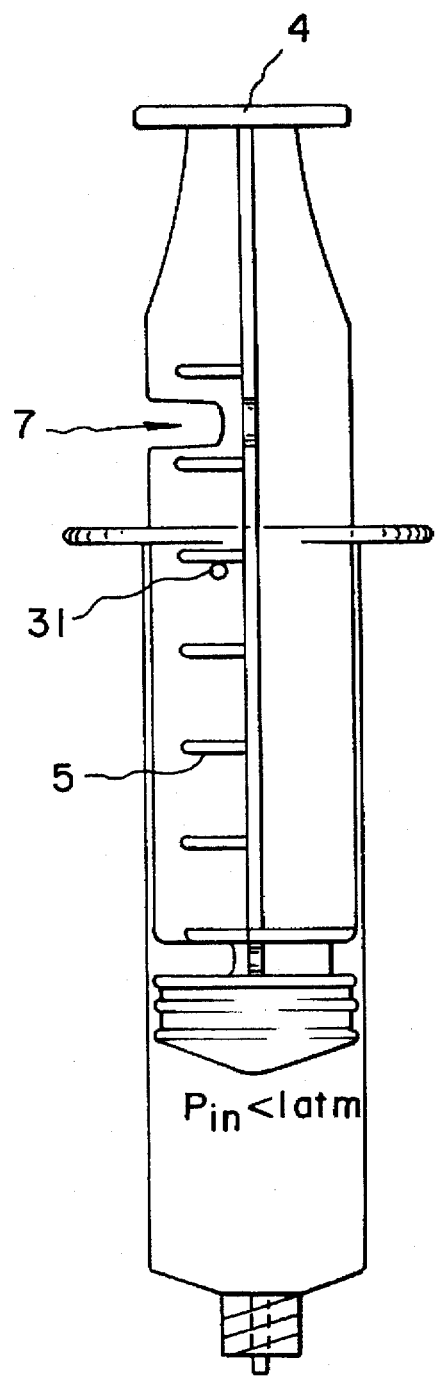
FIG. 7 is a side-elevational view of a plunger inserted into the barrel in a vacuum-type locked position, but with the removable locking pin left off for clarity.

Alternately, the locking means is defined into what may be considered a locked position when the stop member 30 is aligned with the solid portion 5 of one of the locking flanges. In such position the stop member 30 is disposed between the plunger head 22 and the solid portion such that the plunger—biased under negative pressure existing within the barrel 12—will be prevented from being moved toward the second end 16 to which the needle is attached. With reference to FIG. 7, we assume that an external pressure of 1 atm prevails. As the plunger 1 is pulled, a vacuum is created in the space formed between the plunger head 2 and the needle orifice. Due to the lower pressure of $P_{in}<1$ atm in the chamber, the outside pressure of $P_{out}=1$ atm would attempt to push the plunger back so as to attain the equilibrium state. The plunger 1, however, has been locked in that it has been rotated (by about 45°) and the stop member 30 has been mated with the corresponding tab 5. As that mechanical lock cannot easily be overcome, the system will attempt to reach its equilibrium by way of equalizing the inner pressure with the outer pressure. Such equilibrium is thus reached when the chamber has been filled or nearly filled with the corresponding fluid.

A similar exchange occurs when the plunger is locked when an overpressure exists in the chamber between the plunger head 2 and the needle orifice, i.e. when $P_{in}>1$ atm. In that case, the system will automatically issue fluid through the needle opening until equilibrium is reached.

The number of flanges 5 to be disposed on the plunger stem may be chosen in accordance with respective requirements. In the case of compressible fluid, a smaller number of flanges will suffice, while in the case of incompressible fluid, a greater number of flanges is advisable.

It is further preferred if the number and spacing of the flanges on the plunger stem corresponds with the volumetric indicia markings on the barrel 12. When the plunger is pulled and locked adjacent to and in registry with any one of the indicia markings which indicates a specific volume of fluid either to be drawn into the interior 18 of the barrel 12 or alternately to be expelled therefrom. A typical unit of volume would be a cubic centimeter. It should be apparent therefore that the plunger head 2 may be removably locked into any position so as to give the medical personnel operating the aspirator assembly the ability to withdraw an accurate volume of fluids from the human body equivalent to any one or plurality of the volume units indicated by the indicia markings 37.

Figures 5A, 5B:
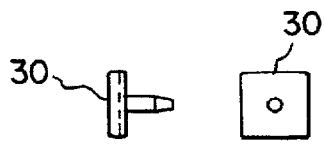
FIGS. 5a, 5b and 5c are side-elevational, front-elevational, and top-plan views, respectively, of a locking pin.
Figure 5C:
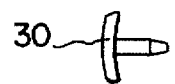

With reference to FIGS. 5a–5c, the stop member 30 is preferably in the form of a plug 30 which is inserted in an opening 31 provided at the top of the barrel 12, after the plunger 2 has been inserted into the barrel interior 18.

In another embodiment of the invention, the stop member 30 is integrally formed on the barrel 12 and it projects inwardly, away from the inner wall surface of the barrel 12.

As illustrated primarily in FIG. 2, the flanges 5 extend across approximately 45° of one of the 90° sectors. The other three sectors are "empty" like conventional prior art devices. When the locking action of the novel device is no longer required or it disturbs proper operation for some reason or another, the plunger is simply rotated by 90° in either direction. The stop member 30 is then aligned with an "empty" sector and the plunger can be reciprocated between the retracted and extended positions without resistance. For that purpose, the plunger stem is provided with cutout openings 7 and 8. In that respect, the plunger 1 as illustrated herein can only be rotated while it is in any of two positions relative to the barrel 12, namely in the fully inserted position (when the cutout opening 7 is aligned with the stop member 30) or in the fully extended position (when the cutout opening 8 is aligned with the stop member).

Figure 8:
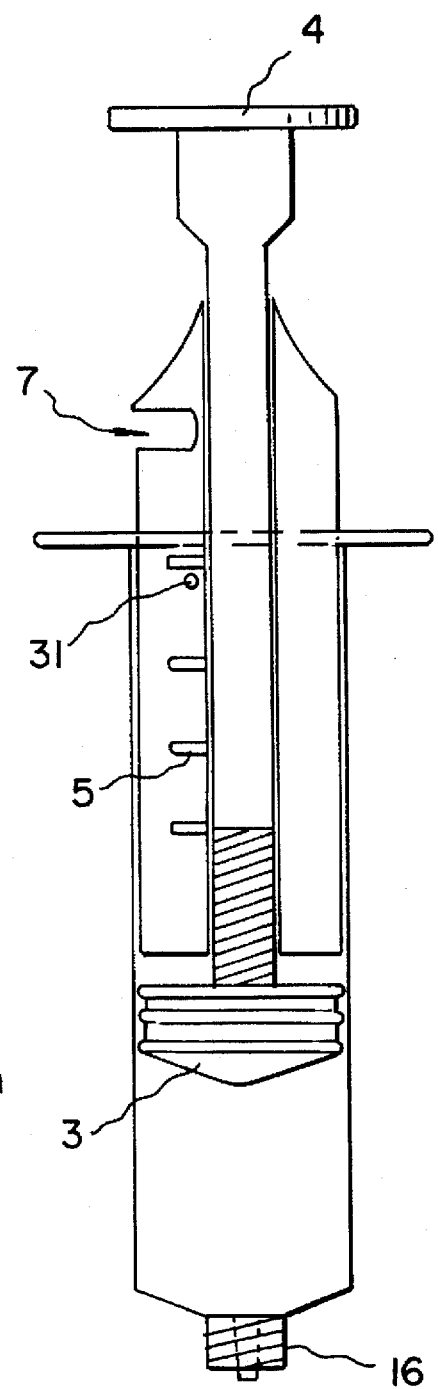
FIG. 8 is a side-elevational view of a second embodiment of the invention.

Referring now to FIG. 8, which illustrates a further embodiment of the invention, the plunger assembly is provided with a fine adjustment in the form of a threaded plunger head screw stem. First, the plunger pressure (positive or negative) is adjusted to an approximate setting by locking at one of the flanges. Secondly, the handle 4 is rotated so as to thread the plunger head until an exact volume is attained in the open space between the plunger and the end 16. This allows for very smooth and accurate adjustment in both dispensing and aspirating.

Figure 9:
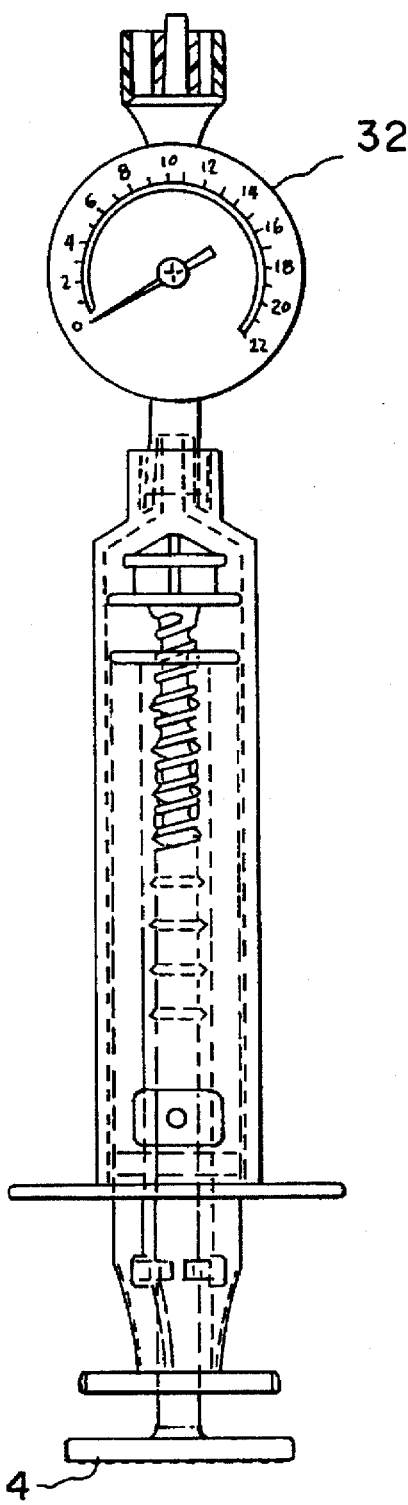
FIG. 9 is a side-elevational view of an alternative embodiment in which the vacuum and the pressure may be accurately determined.
Figure 10:
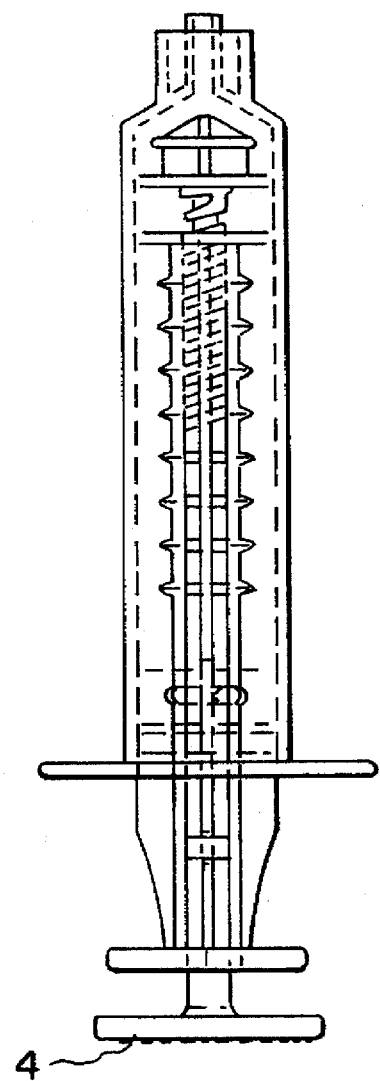
FIG. 10 is a transparent, side-elevational view of the embodiment of FIG. 8.

With reference to FIG. 9, a pressure gauge 32, which is connected in-line at the forward aspirator end, allows even more accurate adjustment of the vacuum or pressure. FIG. 10 illustrates the same plunger without the pressure gauge.

Figure 11:
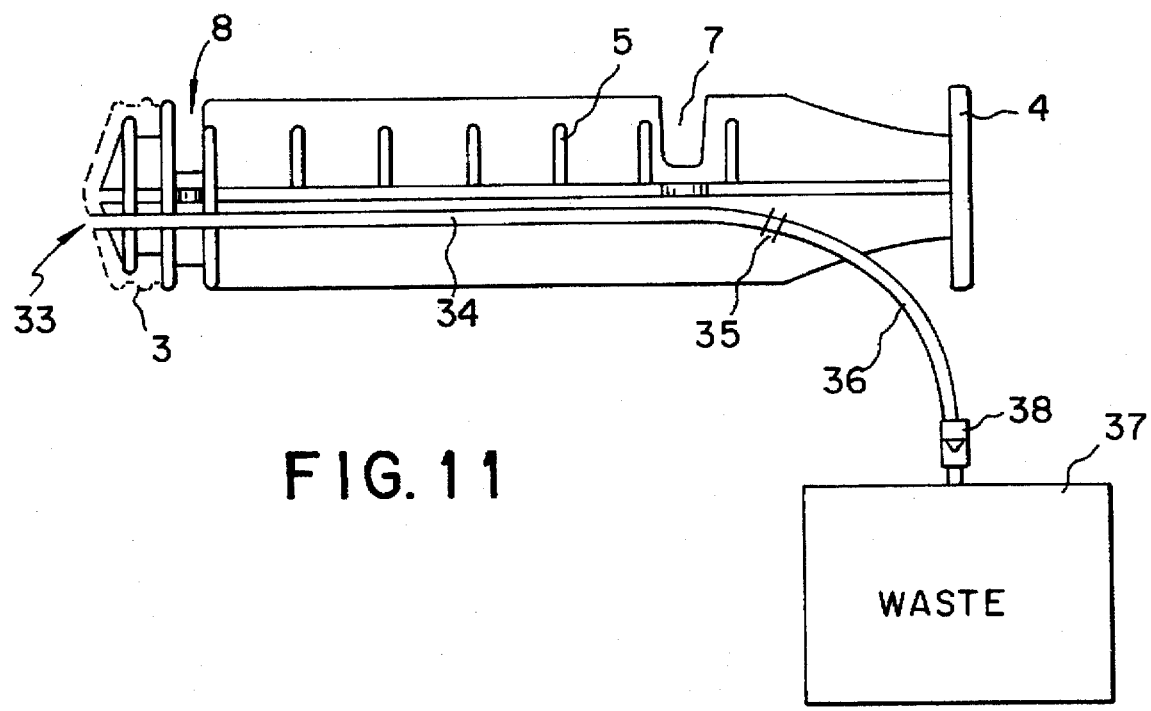
FIG. 11 is a side-elevational view of an alternative embodiment of the plunger and a waste bag attached thereto.

With reference to FIG. 11, a waste port 33 may be provided in the plunger head 3. The waste port 33 communicates through a port passage 34 with a diagrammatically indicated connector (e.g. a luer lock) 35, through a further conduit line 36 with a waste container 37. A one-way valve or a check valve 38 may be disposed inline in the conduit line 36 which prevents spillback of the aspirated waste into the aspirator.

Figure 12:
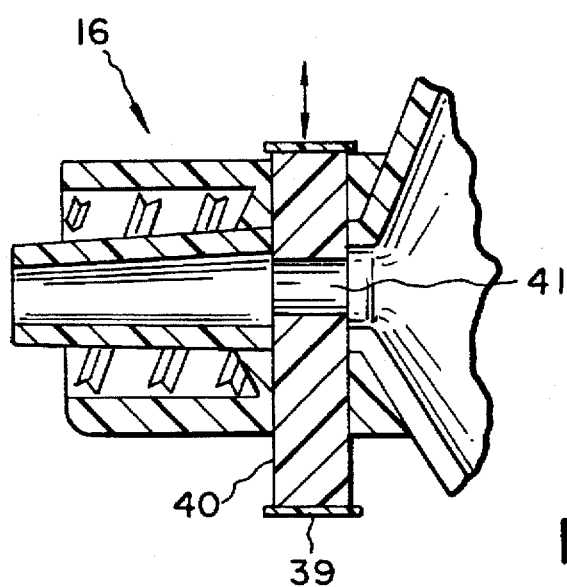
FIG. 12 is a fragmentary view of a forward end of an alternative embodiment of the barrel with a flow control valve.

With reference to FIG. 12, a flow control piston 39 is incorporated in this embodiment in the forward portion of the barrel body. The flow control valve 39 is formed with a cylindrical piston 40 which has an flow opening 41 formed therein. As the piston 40 is pushed transversely to the longitudinal axis of the barrel, the opening 41 aligns with the flow conduit between the luer lock 16 and the barrel interior (open position), or the opening is moved outside the flow conduit, and the cylindrical piston 40 closes the flow conduit (closed position). Among other advantages, the flow control valve 39 allows fluids to be safely stored in the aspirator barrel (e.g. infectuous fluids).

The combination of the embodiments shown in FIGS. 11 and 12 allows the following procedure: In the context of fluid or cyst aspiration, surgical drainage and air evacuation, a vacuum may be first established in the aspirator barrel with the flow control valve 39 closed. After the catheter or syringe have been placed in the region to be drained from the patient, the control valve 39 is opened, and the fluid is aspirated into the barrel body. When the vacuum is (nearly) lost, i.e. the barrel body is filled with fluid, the medical worker closes the flow control valve 39 and pushes the plunger forward, into the barrel. This causes the fluid to flow through the conduit line 34, 35, 36, 38 into the waste container 37. After the barrel has been emptied in this way, the vacuum is reestablished by pulling the plunger and locking it in its position. The waste is thereby prevented from flowing out of the waste container 37 by the one-way valve 38. At this point, the flow control valve 39 is reopened, and the drainage operation is allowed to continue. These steps may be repeated until a sufficient amount of fluid has been drained. The flow control valve 39 may be in the form of an automatic one-way valve, i.e. a check valve, so as to allow flow through the forward end of the barrel only in one direction.

We claim:

1. An aspirator assembly, comprising:
   a) an elongated hollow barrel having a first open end, a second open end with a lock adapted to have an auxiliary device attached and secured thereto, an interior and an interior surface;
   b) a plunger being reciprocally movable within said barrel along a length thereof;
   c) said plunger including an elongated stem having an outer end and an inner end, a grip attached to said stem at said outer end, and a plunger head attached to said stem at said inner end, said plunger head being disposed inside said barrel and being slidably disposed in sealing engagement with said interior surface of said barrel;
   d) locking means selectively positionable into and out of a locked position and formed in part on both said barrel and said stem and adapted for removably locking said plunger head in a plurality of spaced apart locations within and along the length of said barrel;
   e) means for selectively disengaging said locking means and for allowing free reciprocating movement between said plunger and said barrel; and
   f) said stem being formed with a thread and said plunger head being threadingly attached to said thread for finely adjusting a position of the plunger head relative to said barrel.

2. The assembly according to claim 1, wherein said locking means comprise a stop member secured to said barrel and projecting inwardly into said interior of said barrel, said stem having spaced apart locations thereon for engaging said stop member, said stop member being adapted to removably and lockingly engage said spaced apart portions of said stem, whereby said plunger head is lockable at any one of a plurality of said spaced apart locations within said barrel.

3. The assembly according to claim 2, wherein said locking means further comprise a plurality of flanges formed along a length of said stem in spaced relation to one another for selectively bypassing and engaging said stop member.

4. The assembly according to claim 3, wherein said locked position is defined by rotation of said stem and one of said flanges adjacent said stop member, into abutting engagement between said one flange and said stop member.

5. The assembly according to claim 3, wherein each of said flanges include an opening therein of sufficient dimension to allow passage therethrough of said stop member, each of said openings being positionable into said stem relative to said barrel and stop member.

6. The assembly according to claim 5, wherein each of said flanges include a solid portion disposed substantially adjacent said opening therein and adapted to engage said stop member to define said locked position of said locking means.

7. The assembly according to claim 6, wherein said stem is selectively movable linearly along at least a majority of the length of said barrel once said openings of said plurality of flanges are disposed in aligned relation with such stop member to allow passage of said stop member therethrough.

8. The assembly according to claim 6, wherein said stem and adjacent ones of said flanges relative to said stop member are rotatable relative to said stop member for positioning said solid portion of said one flange into abutting engagement with said stop member to define said locked position of said locking means.

9. The assembly according to claim 6, wherein said plurality of flanges comprises a first flange formed on said stem adjacent said plunger head and disposed and adapted for locking engagement with said stop member and disposition of said plunger head adjacent said first open end of said barrel; said stem and said barrel having mid portions; a second flange disposed substantially on said mid portion of said stem and disposed and adapted for locking engagement with said stop member and disposition of said plunger head adjacent said mid portion of said barrel.

10. The assembly according to claim 9, wherein said locked position is defined by rotation of said stem and one of said flanges adjacent said stop member, into abutting engagement with said stop member.

11. The assembly according to claim 6, wherein said plurality of flanges are formed along at least a majority of the length of said stem in equally spaced relation to one another.

12. The assembly according to claim 11, wherein said plurality of flanges are spaced a pre-determined distance from one another sufficient to locate said plunger head at any one of a plurality of spaced apart locations sufficient to equal one cubic centimeter material on markings indicia of said barrel.

13. The assembly according to claim 6, wherein said stem includes a centrally disposed elongated partition integrally formed thereon and extending along the length thereof, each of said plurality of flanges being integrally formed on said partition and extending outwardly therefrom in transverse orientation to the length of both said stem and said barrel.

14. The assembly according to claim 13, wherein said stop member is integrally formed on said interior surface of said barrel and projects therefrom inwardly into said barrel, said stop member disposed and dimensioned to either pass through said opening in an adjacently positioned one of said plurality of flanges or engage said solid portion thereof upon rotation of said stem relative to said stop member.

15. The assembly according to claim 1, wherein said disengaging means are in the form of said stem having cutout openings formed therein for allowing rotation thereof beyond a point at which said stem would otherwise be stopped against rotation by said stop member.

16. The assembly according to claim 1, which further comprises a flow control valve disposed at said second open end of said barrel for selectively closing said second open end.

17. The assembly according to claim 1, wherein said plunger head has a waste port opening formed therein, and including a conduit communicating with said waste port opening and a waste container communicating with said conduit.

18. In an aspirator assembly of the type having an elongated hollow barrel with a first open end and a second open end adapted to be attached at an auxiliary device; a plunger received in the hollow barrel through the first open end and being reciprocatingly movable within the barrel; the plunger including an elongated stem and a plunger head attached to the stem and being slidably disposed in sealing engagement with an interior surface of the barrel, wherein the improvement comprises:

locking means for selectively locking said elongated stem and said plunger head in any one of a plurality of spaced-apart positions along a length of said barrel, and disengaging means for disengaging said locking means and for allowing free reciprocating movement of the plunger with the barrel; and adjusting means for finely adjusting a position of said plunger head relative to said barrel.

19. The assembly according to claim 18, wherein said locking means include a stop member attached to said barrel and locking tabs integrally formed on said elongated stem, and wherein said plunger is rotatable relative to said barrel so as to move said stop member and one of said tabs into a locking position thereof.

20. The assembly according to claim 19, wherein said stop member is removably attached to said barrel.

21. The assembly according to claim 18, wherein said adjusting means includes a threaded stem connected to a rotatable handle, said rotatable handle and said threaded stem cooperating for finely adjusting a position of the plunger head relative to the barrel.

22. The assembly according to claim 18, which further comprises a flow control valve disposed at the second open end of the barrel for selectively closing the second open end.

23. The assembly according to claim 18, wherein said plunger head has a waste port opening formed therein, and including a conduit communicating with said waste port opening and a waste container communicating with said conduit.

* * * * *